United States Patent
Takeuchi et al.

(10) Patent No.: US 11,263,481 B1
(45) Date of Patent: Mar. 1, 2022

(54) AUTOMATED CONTRAST PHASE BASED MEDICAL IMAGE SELECTION/EXCLUSION

(71) Applicant: International Business Machines Corporation, Armonk, NY (US)

(72) Inventors: Yusuke Takeuchi, Boston, MA (US); Benedikt Graf, Charlestown, MA (US); Yiting Xie, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 17/160,961

(22) Filed: Jan. 28, 2021

(51) Int. Cl.
| | |
|---|---|
| *G06K 9/62* | (2006.01) |
| *G06K 9/00* | (2006.01) |
| *G06K 9/46* | (2006.01) |
| *A61B 8/08* | (2006.01) |
| *A61B 5/055* | (2006.01) |
| *A61B 6/00* | (2006.01) |

(52) U.S. Cl.
CPC ....... *G06K 9/6255* (2013.01); *G06K 9/00362* (2013.01); *G06K 9/4647* (2013.01); *G06K 9/6286* (2013.01); *A61B 5/055* (2013.01); *A61B 6/5223* (2013.01); *A61B 8/523* (2013.01); *G06K 2209/05* (2013.01)

(58) Field of Classification Search
None
See application file for complete search history.

(56) References Cited

U.S. PATENT DOCUMENTS

| | | |
|---|---|---|
| 2009/0090873 A1 | 4/2009 | Sapp et al. |
| 2009/0190840 A1 | 7/2009 | Gundel |
| 2011/0002520 A1 | 1/2011 | Suehling et al. |
| 2015/0039553 A1* | 2/2015 | Becker ............... A61B 6/54 706/52 |

OTHER PUBLICATIONS

Lee, Ho Hin et al., "Semi-Supervised Multi-Organ Segmentation through Quality Assurance Supervision", https://arxiv.org/abs/1911.05113, submitted on Nov. 12, 2019, 7 pages.
Muhamedrahimov, Raouf et al., "Learning Interclass Relations for Image Classification", https://arxiv.org/abs/2006.13491, submitted on Jun. 24, 2020, 10 pages.

(Continued)

*Primary Examiner* — David Perlman
(74) *Attorney, Agent, or Firm* — Stephen J. Walder, Jr.; Kelsey Skodje

(57) ABSTRACT

Mechanisms are provided for determining a measure of radiodensity of anatomical structures of interest and classifying medical imaging study data structures (studies) with regard to contrast phase. In some embodiments, this classification may be used to select/exclude slices for processing by other downstream computing systems. A subset of slices are selected from the study and, for each slice in the subset, a corresponding body part regression (BPR) score is determined. A linear regression on the BPR scores is performed and a representative slice is selected based on results of the linear regression. The representative slice is segmented and a statistical measure of a radiodensity metric for each segment in the representative slice is determined.

20 Claims, 7 Drawing Sheets

(56) References Cited

OTHER PUBLICATIONS

Muhamedrahimov, Raouf et al., "Learning to Understand Intravenous Contrast in CT", Proceedings of Machine Learning Research—Under Review: 1-10, 2019, Full Paper—MIDL (Medical Imaging with Deep Learning) 2019 submission, 2019, 13 pages.

Philbrick, Kenneth A. et al., "What Does Deep Learning See? Insights From a Classifier Trained to Predict Contrast Enhancement Phase From CT Images", American Journal of Roentgenology, AJR:211, Dec. 2018, 10 pages.

Sofka, Michal et al., "Automatic Contrast Phase Estimation in CT Volumes", In International Conference on Medical Image Computing and Computer-Assisted Intervention (MICCAI 2011), Sep. 18-22, 2011, 9 pages.

Tang, Yucheng et al., "Contrast Phase Classification with a Generative Adversarial Network", https://arxiv.org/abs/1911.06395; submitted on Nov. 14, 2019, 8 pages.

Yan, Ke et al., "Unsupervised Body Part Regression Via Spatially Self-Ordering Convolutional Neural Networks", 2018 IEEE 15th International Symposium on Biomedical Imaging (ISBI 2018), Apr. 4-7, 2018, 4 pages.

Yellapragada, Manikanta S. et al., "Deep Learning Based Detection of Acute Aortic Syndrome in Contrast CT Images", 2020 IEEE 17th International Symposium on Biomedical Imaging (ISBI), Apr. 3-7, 2020, 4 pages.

\* cited by examiner

AUTOMATED CONTRAST PHASE BASED MEDICAL IMAGE SELECTION/EXCLUSION

BACKGROUND

The present application relates generally to an improved data processing apparatus and method and more specifically to mechanisms for improving computer aided diagnosis (CAD) by providing automated mechanisms for selection/exclusion of medical images upon which CAD is executed based on an automated classification of contrast phase.

Contrast dye, also sometimes referred to as medical imaging contrast, contrast materials, or contrast agent, is a substance that radiologists use to make soft tissue anatomical structures more clearly identified within medical images. That is, in computed tomography, for example, dense substances, such as bones and the like, are easy to see in the medical images, however soft tissues do not show up as well in the images and may look faint. By introducing a contrast dye, or simply "contrast material" hereafter, these tissues are made more visible due to the fact that the contrast material blocks the x-rays and appears white in the medical image, thereby highlighting the blood vessels, organs, or other soft tissue anatomical structures.

One example of a contrast material based medical imaging technique that may be implemented is computed tomography angiography (CTA) in which an injection of contrast material into the blood vessels followed by a CT scan is used to help diagnose and evaluate blood vessel disease or related conditions, such as aneurysms or blockages. Another example is computed tomography pulmonary angiogram (CTPA) in which the contrast material is used to enhance the pulmonary trunk and its branches as part of a diagnostic examination to exclude pulmonary emboli.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system, specially configured to implement a processing pipeline comprising a first trained machine learning model that performs body part regression processing on a medical imaging study data structure, and a second trained machine learning model that performs segmentation of a representative slice selected from the medical imaging study data structure. The method comprises selecting, by a slice extraction engine of the processing pipeline, a subset of slices from the medical imaging study data structure, and generating, by the first trained machine learning model of the processing pipeline, for each slice in the subset of slices, a corresponding body part regression score. The method further comprises performing, by the first trained machine learning model of the processing pipeline, a linear regression on the body part regression scores for the subset of slices, and selecting, by a representative slice selection engine of the processing pipeline, a representative slice from the medical imaging study data structure based on results of the linear regression. In addition, the method comprises processing, by the second trained machine learning model of the processing pipeline, the representative slice to segment the representative slice and generate a statistical measure of a radiodensity metric for each segment in the representative slice. In this way, a small subset of slices need only be processed through the automated computing tool mechanism of the illustrative embodiments in order to determine the statistical measure of radiodensity metric for anatomical structures of interest in a medical imaging study data structure, thereby reducing resource costs and improving the speed or timing of processing medical imaging studies.

In some illustrative embodiments, selecting the representative slice from the medical imaging study data structure comprises selecting a slice index, from a plurality of slice indices for slices in the medical imaging study data structure, corresponding to a slice having a body part regression score closest to a known body part regression score for a slice depicting an anatomical structure of interest, as the representative slice. In this way, a single representative slice may be selected using linear regression of body part regression scores such that only a single slice need be segmented in order to identify anatomical structures of interest and their corresponding measures of radiodensity, indicative of whether a contrast material is present or not.

In some illustrative embodiments, the method further comprises comparing, for at least one segment in the representative slice, a corresponding statistical measure of radiodensity metric to a threshold radiodensity metric, determining whether or not sufficient enhancement by a contrast material is present in the representative slice in response to results of the comparison, and generating an output based on results of determining whether sufficient enhancement by a contrast material is present or not in the representative slice. In this way, the illustrative embodiments provide an automated computer tool that is able to determine if sufficient enhancement by a contrast material is present in the images of a medical imaging study to ensure that a computer aided diagnosis system will be able to generate accurate results should the medical imaging study data structure be input to the computer aided diagnosis system. Hence a filtering of medical imaging study data structures may be performed and computer aided diagnosis system resources may be more efficiently utilized.

In some illustrative embodiments, determining whether or not sufficient enhancement by a contrast material is present in the representative slice further comprises determining that sufficient enhancement is present in response to the comparison indicating that the statistical measure of radiodensity metric meets or exceeds the threshold radiodensity metric, and determining that insufficient enhancement is present in response to the comparison indicating that the statistical measure of radiodensity metric does not meet or exceed the threshold radiodensity metric. In this way, the illustrative embodiments may determine whether contrast material is present in the anatomical structures of interest in the representative slice, since such contrast material will be represented as pixels with intensities or grayscale coloring having values corresponding to radiodensity metrics above a threshold value.

In some illustrative embodiments, in response to the determination indicating that there is sufficient enhancement, generating the output comprises inputting at least a portion of the medical imaging study data structure to a downstream computer aided diagnosis (CAD) computing system for processing of the at least a portion of the medical imaging study data structure. Thus, again, a filtering of medical imaging study data structures is provided such that only those medical imaging study data structures having sufficient enhancement are processed by the downstream CAD computing system.

In some illustrative embodiments, the downstream CAD computing system is one of a plurality of downstream CAD computing systems, each CAD computing system in the plurality of downstream CAD computing systems comprising a corresponding trained machine learning computer model trained to perform computer aided diagnosis evaluations for different anatomical structures. In this way, medical imaging study data structures may be routed to the corresponding CAD computing systems for which the medical imaging study data structures have sufficient enhancement present.

In some illustrative embodiments, the portion of the medical imaging study data structure comprises a subportion of indexed slices in the medical imaging study data structure, less than a total number of indexed slices in the medical imaging study data structure, wherein the subportion comprises a predetermined number of slices having indices greater than or lower than an index of the representative slice. Thus, in some illustrative embodiments, not all of the slices of a medical imaging study data structure need be processed by the downstream CAD computing system and only a sub-portion that corresponds to those slices most likely to have the anatomical structure of interest sufficiently enhanced maybe sent to the downstream CAD computing system, again improving resource utilization and speed of processing.

In some illustrative embodiments, in response to the determination indicating that there is not sufficient enhancement, generating the output comprises generating an alert notification to a computing device or display device to output a notification indicating that processing of the medical imaging study data structure by a downstream computer aided diagnosis computing system will generate inaccurate results due to insufficient contrast material enhancement. In this way, human operates may be informed that if they processed with downstream CAD computing system processing, the results may not be reliable and the human being may have to make a judgement call as to whether the results of the CAD system can be relied upon.

In some illustrative embodiments, generating the output based on results of determining whether sufficient enhancement by a contrast material is present or not in the representative slice further comprises classifying the medical imaging study data structure into one of a plurality of contrast phase classifications based on the results of determining whether sufficient enhancement by a contrast material is present or not. In this way, the automated improved computing tool may be able to determine what contrast phases are represented in medical imaging study data structures and may classify them accordingly. In some illustrative embodiments, the medical imaging study data structure may then be annotated in metadata of the medical imaging study data structure so as to make explicit in the metadata the determined contrast phase(s) represented in the slices of the medical imaging study data structure.

In some illustrative embodiments, the body part regression score for a given slice is a value indicative of a relative physical distance between the given slice and a slice comprising a depiction of an anatomical structure of interest. The body part regression score provides a mechanism for performing linear regression on a small subset of slices so as to select a representative slice used to classify the medical imaging study data structure with regard to contrast phase.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
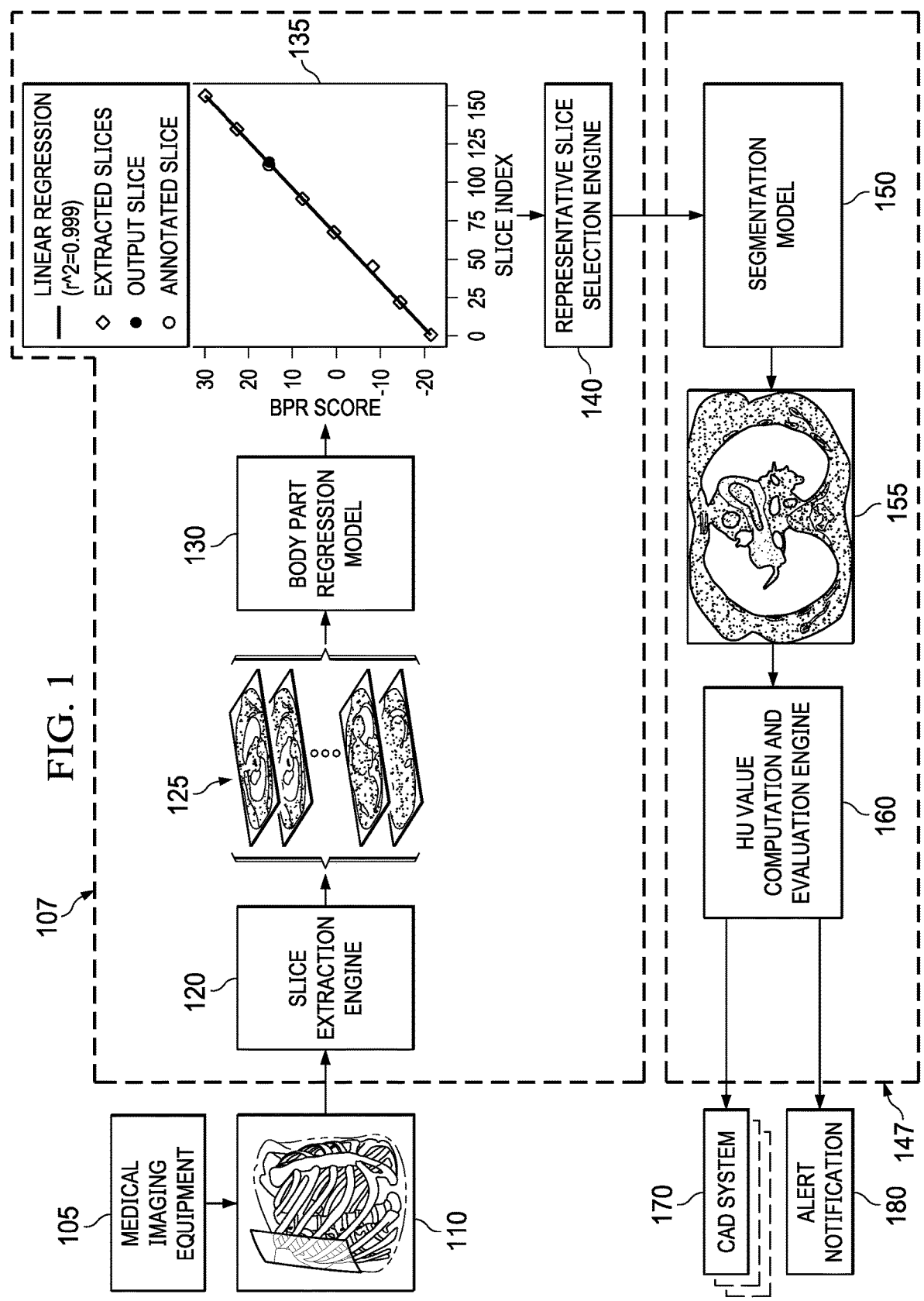
FIG. 1 is an example diagram showing a processing flow of a processing pipeline in accordance with an improved computing tool of one illustrative embodiment.

As mentioned previously, various types of medical imaging techniques make use of contrast materials to enhance soft tissue anatomical structures, e.g., CTA and CTPA. During a medical imaging study, many hundreds of individual medical images are taken, over a continuous period of time, of the three-dimensional anatomical structures of the patient. Because the anatomical structures of the patient are working structures, it takes time for the contrast material to move throughout the body of the patient and reach areas of interest. Thus, some images may not include contrast material enhanced images while others may at various times during the continuous time range of the particular medical imaging study. In the past, the resulting images, e.g., hundreds of individual two dimensional medical images, or "slices", generated as part of a contrast material enhanced medical imaging study were presented to a human radiologist for them to browse and hopefully accurately identify anomalies if any are present. Such manual approaches were subject to error due to human limitations, costly in terms of time, human resources, and consequences with regard to misdiagnosis, and highly dependent on the particular human being's own experience and knowledge.

To assist human beings with evaluating medical images captured through such medical imaging technology, computer aided diagnosis (CAD) systems may be utilized. CAD systems employ artificial intelligence (AI), computer vision, and image processing computer systems to enhance the medical images, identify structures within the medical images, generate measurements of structures within the medical images, and assist human beings with identification of abnormalities depicted in the medical images. While CAD systems do not replace the judgement of the human expert, e.g., human radiologist, they do provide a powerful tool to assist the human expert in making the final determination of whether a patient has anomalous or potentially problematic conditions that should be treated.

For CAD systems to provide accurate results, it is important that the medical images input to, and processed by, the CAD systems be of high quality with regard to contrast material enhancement for the particular diagnoses the CAD system is trained to assist with. That is, if a CAD system is assisting with a CTA scan for diagnosing anomalies or diseases associated with aneurysms or blockages, then it is important that the medical images the CAD system processes be contrast material enhanced to allow the CAD system to more accurately identify such anomalies or diseases. Similarly, if the CAD system is assisting with a CTPA scan for diagnosing anomalies or diseases associated with pulmonary emboli, then the medical images the CAD system processes should be contrast material enhanced in the appropriate organs and soft tissues, e.g., the pulmonary trunk and its branches, to allow the CAD system to more accurately identify such anomalies or diseases. If the input medical images of an imaging study comprise images where the contrast material enhancement is not present in the anatomical structures of interest, then the accuracy of the results will be diminished since such images will cause the CAD system to more likely indicate no abnormalities present, e.g., any lesions will not be detected. This is the case even if some of the medical images of the medical imaging study have contrast material enhancement in the appropriate anatomical structures of interest.

However, the input medical imaging study data structure does not document the contrast phase of the medical imaging study. That is, the input medical imaging study data structure may be a Digital Imaging and Communications in Medicine (DICOM) where metadata is provided that documents various characteristics of the patient who is the subject of the medical imaging study, some characteristics of the equipment used to capture the medical images may be specified, and some settings characteristics may be provided to specify how the equipment was configured for capturing the medical images. However, the particular contrast phase depicted in the medical images is not usually documented in this metadata of the input medical imaging study data structure. The "contrast phase" refers to the portion a period of time after contrast material is injected into the patient, where the different phases correspond to different levels/regions of tissue enhancement, e.g., see radiologyassistant.nl/more/ct-protocols/ct-contrast-injection-and-proto-cols. For example, CTPA is one of the contrast phases where the pulmonary artery is enhanced, e.g., 6-13 seconds after injection.

Thus, when a medical imaging study data structure, e.g., DICOM data structure, is input to a CAD system, the CAD system is not made aware of the particular contrast phase, if any, represented in the medical images of the medical imaging study data structure. Thus, the CAD system may be trained on contrast material enhanced medical images and as such, expect that the medical images input to the CAD system have similar contrast material enhanced medical images. However, if the input medical images do not have the contrast material enhancement, or there is not enough contrast material enhancement in the collection of medical images in the medical imaging study data structure, the CAD system may generate inaccurate results, assuming that there are no abnormalities, e.g., lesions, since they were not enhanced sufficiently in the medical imaging study data structure.

In view of the above, it would be beneficial to be able to automatically determine whether a medical imaging study data structure comprises medical images with appropriate contrast material enhancement for use by a trained CAD system prior to inputting the medical imaging study data structure into the trained CAD system. That is, it would be beneficial to determine whether the medical imaging study data structure represents an appropriate contrast phase for the trained CAD system. In order to classify medical imaging studies, or "scans", based on contrast phases, detecting the Hounsfield Unit (HU) values has been determined to be the most appropriate approach. That is, contrast phases are continuous and thus, it is difficult to distinguish the line between phases. In order to determine a specific contrast phase, one can look at which, and how much, blood vessels in a medical image are enhanced. After the injection of a contrast material, an increase in CT attenuation is achieved, which is characterized by HU values in the CT. The degree of increase in contrast enhancement is described by the change in HU values. However, in order to detect the HU values in a useful manner, it is important to extract a specific slice from the medical imaging study that likely has the anatomical structures of interest represented in the extracted slice.

The Hounsfield Unit (HU) scale is a quantitative scale for describing radiodensity, and is often used in computed tomography (CT) scans where its value may also be referred to as a CT number. The HU scale is a linear transformation of the original linear attenuation coefficient measurement into one in which the radiodensity of distilled water at standard temperature and pressure (STP) is defined as zero HU, while radiodensity of air at STP is defined as −1000 HU. A change of one HU represents a change of 0.1% of the attenuation coefficient of water since the attenuation coefficient of air is nearly zero. By determining the HU value, or CT number, and assigning thresholds to various tissues and anatomical structures, the visualization of the anatomy of a patient is made possible by defining different shades of gray for different types of tissues. The same is true of contrast materials which will also have their own thresholds or ranges of HU values that indicate the presence of a contrast material in the portion of the patient's body being imaged. For example, if the HU value in the pulmonary artery is higher than a threshold of 200, then it can be determined that the medical imaging study (or "scan") has a CTPA contrast phase and thus, the medical imaging study data structure can be used by downstream computer aided diagnostic (CAD) systems configured to diagnose pulmonary emboli.

Thus, if one were able to select a medical image within a medical imaging study that most likely comprises the anatomical structures of interest for a particular CAD system operation, and then analyze the medical image to determine the HU values for anatomical structures present in the selected medical image to determine if the selected medical image has a contrast material present within the medical image, then one could determine that the medical imaging study data structure comprises medical images having sufficient contrast material enhancement of the appropriate anatomical structures to warrant processing by the CAD system. In such a case, the medical imaging study data structure as a whole, or a subset of medical images associated with the selected medical image, e.g., a predetermined range of medical image slice indices before/after the selected medical image, may be selected for processing by the CAD system. If the selected medical image does not have sufficient contrast material enhancement, a notification may be output to a human operator to indicate the potential for lower accuracy in CAD system operation and/or the medical imaging study data structure may not be input to the CAD system for processing.

The present invention provides such an automated improved computing tool that operates on medical imaging studies to select a medical image slice from the medical imaging study, evaluate the HU values of anatomical structures in the selected medical image slice, classify the medical imaging study data structure with regard to a target contrast phase for the CAD system, and perform appropriate actions based on the classification of the medical imaging study data structure. In one illustrative embodiment, the automated improved computer tool of the present invention automatically, and efficiently, detects HU values in anatomical structures, such as blood vessels, from a selected axial slice. The selected axial slice is automatically selected and extracted from the medical imaging study data structure, or scan, and is then used to determine whether the medical imaging study data structure should be processed by specific downstream CAD systems. Artificial Intelligence (AI) mechanisms are provided for selecting the axial slice (in a first stage of operation) and segmenting the selected axial slice (in a second stage of operation) such that HU value detection is performed on the resulting segmented anatomical structures represented in the selected slice. The HU values will indicate whether a contrast material is present or not in the selected slice and thus, will indicate whether the medical imaging study comprises contrast material enhancement in the area of the anatomical structures of interest to the particular diagnoses being evaluated.

In some illustrative embodiments, this process may be performed with regard to various different anatomical structures of interest and the corresponding results of the evaluation may be used to route the medical imaging study to an appropriate CAD system in a plurality of CAD systems. For example, there may be two CAD systems provided, one for processing CTA medical imaging studies and one for CTPA medical imaging studies. A medical imaging study data structure may be provided which does not specify in the metadata of the medical imaging study data structure what the contrast phase is for the medical imaging study. The mechanism of the illustrative embodiments may evaluate the medical imaging study, by applying medical image slice selection logic, HU value detection logic, and contrast phase classification logic to determine if the medical imaging study data structure comprises medical images in which the anatomical structures for accurate CTA processing by a CTA CAD system are sufficiently enhanced with contrast material. Similarly, consecutively or in parallel, the mechanisms of the illustrative embodiments may evaluate the medical imaging study, by applying medical image slice selection logic, HU value detection logic, and contrast phase classification logic to determine if the medical imaging study data structure comprises medical images in which the anatomical structures for accurate CTPA processing by a CTPA CAD system are sufficient enhanced with contrast material. Based on the results of these classifications, the medical imaging study data structure may be routed to one of the CTA or CTPA CAD systems for appropriate processing, e.g., diagnosing pulmonary emboli in the case of a CTPA CAD system.

The selection of the axial slice may be performed by evaluating a subset of slices spanning a range of slice indices of the medical imaging study, perform a linear regression on the range of slice indices with regard to a body part regression (BPR) score, and select a slice index that is closest to a known BPR score for a medical image comprising a particular anatomical structure of interest. A deep learning or convolutional neural network (DNN or CNN) model, or other artificial intelligence (AI) computer model that may be trained to recognize BPR scores, is trained to predict BPR scores for medical image slices, perform linear regression on BPR scores for a selected small subset of medical image slices from the medical imaging study data structure, and select a medical image slice whose BPR score is closest to the known BPR score for a medical image comprising the anatomical structure of interest, as determined from the results of the linear regression, as will be discussed in greater detail hereafter.

After having selected the axial slice, in a second stage of operation, the mechanisms of the illustrative embodiments may apply a trained segmentation computer model, which may be another DNN, CNN, or other AI computer model trained to perform medical image segmentation to identify the contours of anatomical structures in the medical image. This segmentation model may be applied to the extracted slice to thereby identify the anatomical structure segmentations within the extracted (selected) slice. For example, anatomical structures, such as various blood vessels including the superior vena cava (SVC), ascending aorta, descending aorta, pulmonary artery, etc., may be identified. Having identified the segmented anatomical structures, e.g., blood vessels, in the extracted slice, a statistical measure of the HU values (CT numbers) for the various anatomical structures may be determined, e.g., a median HU value may be determined from the HU values, captured and calculated by the CT equipment when generating the medical imaging study data structure, that are present within the contours (segments) of the anatomical structures of interest. The HU values may be used to identify whether particular anatomical structures, e.g., blood vessels, have contrast materials present or not in the extracted (selected) slice. Based on this determination of whether contrast materials are present in the extracted slice, which is determined to be the slice most likely to have the anatomical structures of interest, the mechanisms of the illustrative embodiments may automatically determine whether the medical imaging study data structure, or scan, comprises medical images with sufficient enhancement from contrast materials to warrant further processing by the corresponding CAD system. As noted above, this can be done for various anatomical structures and for various trained CAD systems so that the medical imaging study data structure, or a subset of the medical images in the medical imaging study data structure, may be routed to an appropriate trained CAD system, or processing by a downstream CAD system may be blocked if it is determined that the medical imaging study data structure does not comprise a sufficient level of enhancement to ensure accurate results from the downstream CAD system.

In addition, it should be appreciated that this process may be repeated for subsets of medical images within the medical imaging study data structure. That is, in a single medical imaging study data structure, there may be medical images taken for various portions of the patient's body which correspond to different contrast phases, but without the particular contrast phases identified in the metadata of the medical imaging study data structure, e.g., there may be a first subset of medical images that correspond to a CTA contrast phase and a second subset of medical images that correspond to a CTPA contrast phase. As the medical imaging is performed with contrast material in a continuous manner, it is not readily discernable where one contrast phase starts/ends and another starts/ends, especially when not denoted in the metadata. Thus, in some illustrative embodiments, a first subset of medical images may be selected and the above process applied to determine if the first subset of medical images comprise medical images for a particular contrast phase. The same process may then be repeated for other subsets of medical images within the medical imaging study data structure. Thus, if the medical imaging study data structure contains more than one contrast phase, these will be identified through the mechanisms of the illustrative embodiments and the portions of the medical imaging study data structure may be routed to appropriate CAD systems based on the determined contrast phase.

It should also be appreciated that the mechanisms of the illustrative embodiments may determine that the medical images of the medical imaging study data structure, or a selected subset of the medical imaging study data structure, do not contain sufficient enhanced anatomical structures, enhanced by contrast materials, to result in accurate processing by the CAD system(s). In such a case, an alert notification can be output to a human user and/or the medical imaging study data structure may not be input to the CAD system(s). With the alert, the human user is informed that if they continue with the processing of the medical imaging study by the CAD system, the results may not be accurate, or at least the accuracy may be reduced, due to insufficient enhancement in the medical images.

In order to perform the evaluation of the medical imaging study data structure to determine whether the medical imaging study data structure comprises sufficiently enhanced medical images for processing by a subsequent CAD system, only a small portion of the medical imaging study data structure need be processed. For example, medical imaging study data structures may comprise hundreds of individual slices, e.g., approximately 200-400 slices. In order to perform the evaluation of the medical imaging study data structure in accordance with the illustrative embodiments, a very small set of selected slices are used to perform the evaluation, e.g., in one illustrative embodiment, only 8 slices are selected to perform the evaluation to select a $9^{th}$ slice that is the slice most likely to comprise the anatomical structures of interest to the particular contrast phase, e.g., a slice comprising the pulmonary trunk for a CTPA contrast phase or the aorta for a CTA contrast phase.

Thus, rather than having to load all 200-400 slices and evaluate all 200-400 slices to determine if there is sufficient enhancement, or rather than having to load all 200-400 slices and process them through the CAD system before determining that the CAD system cannot provide accurate results, the illustrative embodiments utilize a trained AI computer model, trained through machine learning processes, to perform linear regression to select a single medical image representative of the medical imaging study data structure which can be used to determine the HU values for segmented structures and determine if there is sufficient enhancement of anatomical structures of interest. This greatly reduces processing resource needs and greatly increases the speed of the process of determining whether accurate results may be obtained from a CAD system. Moreover, this reduces CAD system resource utilization since expenditure of such resources may be saved on medical imaging study data structures that do not have sufficient enhancement to ensure accurate results by the trained CAD system. In addition, the mechanisms of the illustrative embodiments provide a measurement, e.g., HU values, that can be used to explain the classification of the medical imaging study with regard to various contrast phases, i.e., the illustrative embodiment can indicate that because the representative image from the medical imaging study did not have a HU value above a particular threshold in a particular anatomical structure, it was not determined to have a particular contrast phase, or if it did have a HU value above a particular threshold, it was classified as having a particular contrast phase.

It should be appreciated that while the illustrative embodiments will be described in the context of the evaluation of HU values to determine contrast phase classifications and for routing medical imaging study data structures to downstream trained CAD systems, or sending alerts if it is determined that downstream CAD systems will likely generate inaccurate results due to a lack of enhancement in the medical imaging study data structures, the illustrative embodiments are not limited to these particular applications of the automated improved computing tool of the present invention. To the contrary, the automated improved computing tool mechanisms of the illustrative embodiments are able to automatically determine the HU values for anatomical structures of interest, where these HU values may then be used for various purposes and various use cases, some of which are those described herein. Any other utilization of the HU values generated by the automated improved computer tool of the illustrative embodiments may be implemented without departing from the spirit and scope of the present invention, as will be readily apparent to those of ordinary skill in the art in view of the present description.

Before continuing the discussion of the various aspects of the illustrative embodiments and the improved computer operations performed by the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a specifically configured computing system, configured with hardware and/or software that is itself specifically configured to implement the particular mechanisms and functionality described herein, a method implemented by the specifically configured computing system, and/or a computer program product comprising software logic that is loaded into a computing system to specifically configure the computing system to implement the mechanisms and functionality described herein. Whether recited as a system, method, of computer program product, it should be appreciated that the illustrative embodiments described herein are specifically directed to an improved computing tool and the methodology implemented by this improved computing tool.

In particular, the improved computing tool of the illustrative embodiments specifically provides automated computer logic and artificial intelligence computer models that are specifically trained through machine learning processes to implement two stages of operation: a first stage of operation directed to selecting an axial slice, i.e. individual two-dimensional image, of an anatomical structure of interest, from a medical imaging study representative of a patient's internal anatomy; and a second stage of operation directed to segmenting the selected slice, compute a statistical measure of the HU values of the anatomical structure of interest, and evaluate the statistical measure of the HU value. In addition, in some illustrative embodiments, as part of this second stage of operation, the statistical measure of the HU value may be used to determine if sufficient contrast material enhancement is present for accurate evaluation by a CAD system. The improved computing tool implements mechanism and functionality, such as one or more machine learning trained computer models and corresponding computer logic trained to predict body part regression (BPR) scores and perform linear regression on such BPR scores to select a slice from the collection of medical images (or slices) present in a medical imaging study data structure and/or segment a selected slice and compute HU values (CT numbers) for anatomical structures of interest, which cannot be practically performed by human beings mentally or with the aid of pen and paper.

The improved computing tool provides a practical application of the methodology at least in that the improved computing tool is able to determine a statistical measure of HU values for particular anatomical structures of interest from a small subset of slices, e.g., 9 out of 200-400 slices. Moreover, the improved computing tool, in some illustrative embodiments, provides a practical application by providing an improvement to the accuracy of CAD systems by eliminating medical imaging studies, or portions of medical imaging studies, that do not have sufficient contrast material enhancement in the anatomical structures of interest to allow the CAD system to generate accurate results. Moreover, the improved computing tool provides a practical application in that the invention improves the loading of medical images into CAD systems by reducing the size of the medical images loaded and thereby increases the speed of the CAD systems both with regard to loading of input data and with regard to the amount of data that the CAD system must process in order to generate results, e.g., rather than loading all of the 200-400 medical images, for example, a subset of medical images corresponding to the selected medical image may be loaded and processed via the CAD system, e.g., X number of slices above and below the selected medical image (slice) in terms of slice index, where X is any desired value that provides a sufficient number of slices to represent the anatomical structure(s) of interest to the diagnoses evaluated by the trained CAD system.

With regard to computer program product embodiments, the computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As outlined above, the illustrative embodiments are directed to an improved computer tool, improved computer tool methodology, and computer program product that provides logic for implementing an improved computer tool on hardware of one or more computing systems, that operates to evaluate a medical imaging study data structure using artificial intelligence to determine if and what type of contrast phase medical images are present and whether the contrast material enhancement, if any, is sufficient for accurate processing of the medical images through a computer aided diagnostic (CAD) system. The improved computer tool includes a first artificial intelligence (AI) mechanism employing one or more machine learning trained computer models, such as DNNs or CNNs, for example, that determines body part regression (BPR) scores and performs linear regression on the BPR scores for selected slices from a medical imaging study data structure and selects a slice that is determined to most likely contain an anatomical structure of interest with regard to a contrast phase corresponding to the types of diagnosis sought, e.g., for a CTPA contrast phase, a slice that is most likely to include the pulmonary trunk and branches. The improved computer tool also includes a second AI mechanism, employing one or more machine learning trained computer models, such as DNNs or CNNs, for example, that perform segmentation on the selected slice to identify anatomical structures of interest, e.g., SVC, ascending aorta, descending aorta, pulmonary artery, etc., present in the selected slice. Based on the segmentation, for each segmented structure, a statistical measure, e.g., median or the like, of the Hounsfield Unit (HU) values for these anatomical structures is determined. In some illustrative embodiments, the statistical measure is compared to ranges of HU values indicative of sufficient contrast material enhancement. If results of the comparison indicate that there is sufficient contrast material enhancement, then the medical imaging study data structure, or a selected portion of the medical imaging study data structure, is provided as input to a corresponding CAD system. If the results of the comparison indicate that there is insufficient contrast material enhancement, then an appropriate notification may be output to a human user and/or the medical imaging study data structure is not input to the CAD system for processing.

In some illustrative embodiments, this process can be performed with regard to different types of contrast material phases, e.g., CTA, CTPA, Delayed, etc. and the medical imaging study data structure may be routed to an appropriately trained CAD system for the corresponding contrast material phase represented in the medical imaging study data structure, as determined by the mechanisms of the illustrative embodiments. Multiple different ones of the first and/or second AI mechanisms may be provided, each trained for evaluating a medical imaging study data structure with regard to different contrast material phases, for example, such that different pipelines of processing may be defined. Each processing pipeline may operate on the same medical imaging study data structure in parallel to evaluate the medical imaging study data structure with regard to different contrast material phases.

Thus, the improved computing tool of the illustrative embodiments provides a mechanism for automatically determining whether an input medical imaging study data structure comprises medical images (slices) which contain sufficient contrast material of a particular desired contrast material phase for accurate processing by a trained CAD system. The improved computing tool performs such operations on a small set of selected medical images (slices) extracted from the medical imaging study data structure and uses linear regression to identify a slice in the medical imaging study that is most likely to include anatomical structure(s) of interest to the particular diagnoses for which the CAD system is trained. The single slice is then segmented, and HU values are computed to determine if a sufficient amount of enhancement is present due to a contrast material. Thus, the improved computing tool only need process a very small set of slices to select a single representative slice for the medical imaging study data structure. Then, that single representative slice is the only slice that needs to be segmented to determine if there is sufficient enhancement. Thus, the improved computing tool provides a very rapid and low resource cost mechanism for determining the HU values for anatomical structures of interest, and contrast phase(s) represented in the medical imaging study data structure, as well as determining if there is sufficient enhancement that a downstream CAD system will be able to generate accurate results. This enhances the performance of the CAD system as well and reduces resource costs of CAD systems by avoiding processing, by the CAD system, of medical imaging studies that do not have sufficient enhancement and will likely result in inaccurate results.

The illustrative embodiments described herein utilize computed tomography (CT) medical imaging and computed tomography pulmonary angiogram (CTPA) as examples. It should be appreciated that the illustrative embodiments are not limited to CT medical imaging or CTPA contrast phase determinations. To the contrary, the mechanisms of the improved computer tool of the illustrative embodiments may be implemented with any medical imaging modality, e.g., U.S. and MiII, and to extract slides and evaluate them with regard to any blood vessels and/or other anatomical structures that may be enhanced by contrast material. For example, a slice that shows the pulmonary artery and the aorta can be extracted for CTPA and CTA, while a slice that shows the kidneys and the abdominal aorta can be extracted for CTA and Delayed phase.

FIG. 1 is an example diagram showing a processing flow of a processing pipeline in accordance with an improved computing tool of one illustrative embodiment. It should be appreciated that each of the stages and sub-stages of the processing pipeline shown in FIG. 1 is implemented in computer logic, either through specially configured hardware elements specifically configured to perform their corresponding computer functions, through configuration of computer hardware by software executed on the computer hardware to specifically configure the computer hardware to perform the corresponding computer functions, or a combination of specially configured hardware elements and/or software configured hardware elements. Moreover, the processing pipeline, or simply "pipeline", shown in FIG. 1 is a single pipeline, however in some illustrative embodiments multiple processing pipelines configured for different contrast phase evaluations and/or CAD systems may be implemented. For purposes of illustration, the pipeline of FIG. 1 will be described hereafter with regard to an example CTPA contrast phase evaluation in which a slice containing the pulmonary trunk is selected, however as noted above, this is only for illustrative purposes and is not intended to state or imply any limitation on the applicability of the mechanisms of the improved computing tool of the illustrative embodiments.

As shown in FIG. 1, medical imaging equipment 105, such as a computed tomography (CT) medical imaging device and associated computing system, generates a medical imaging study data structure 110 that represents the three dimensional scan of a patient's internal anatomy in a manner generally known in the art. The three dimensional scan may comprise a plurality of two dimensional images that are combined to generate the three dimensional representation of the internal anatomy, each two-dimensional image being a "slice" of the three-dimensional anatomy. The medical imaging study data structure 110 may comprise many hundreds (e.g., 200-400) or more of these slices, indexed by slice number indicating a slice's position within a sequence of slices along an axis. Each slice is comprised of the Hounsfield Unit (HU) values or CT numbers for pixels of the image that can be used to represent the data as images on a computer screen with varying gray-scale coloring, or intensities, of the pixels in accordance with the HU values or CT numbers. The HU values or CT numbers are pixel values in CT image data generated by the CT imaging and computer equipment in a manner generally known in the art.

In some illustrative embodiments, the medical imaging study data structure may comprise medical images for a plurality of contrast material phases, e.g., CTA, CTPA, Delayed, etc. as the medical imaging study, or scan, may be performed of a period of time where the contrast material is circulated through the patient's blood stream to various portions of the anatomy that is then captured in medical imaging. However, as discussed above, the medical imaging study data structure 110, which may be a DICOM data structure for example, may not include metadata that specifies the particular contrast material phases captured during the scan.

The medical imaging study data structure 110 from the medical imaging equipment 105 is provided as input to a first stage of operation 107 of the processing pipeline 100 that comprises the slice extraction engine 120, the body part regression computer model 130, and representative slice selection engine 140. The slice extraction engine 120 comprises computer logic that executes functions to extract a subset of slices from the medical imaging study data structure 110. The selection of the subset of slices may take many different forms and the selection may be based on many different criteria depending on the desired implementation. For example, the selection of a subset of slices may comprise selecting a predetermined number of slices over a predetermined range of slices of the medical imaging study data structure, where the number of slices selected and the range of slices over which the selection is performed is based on a balancing of performance factors, such as computational resources required, loading time, processing time, etc. versus accuracy of the evaluation of the subset of slices, e.g., accuracy in the linear regression described hereafter for selection of a representative slice from the medical imaging study data structure 110. For example, in one illustrative embodiment, 8 slices are selected from the medical imaging study data structure 110. The selected slices preferably are evenly spaced across the range of slices in the medical imaging study data structure in order to generate more accurate linear regression results, however this is not a requirement and any subset of slices may be selected depending on the desired implementation. For example, in a medical imaging study data structure comprising 400 slices in total, slices having slice indices 0, 57, 114, 171, 228, 285, 342, and 399 may be extracted for use in performing the linear regression.

Thus, the slice extraction engine 120 selects a subset 125 of slices from the medical imaging study data structure 110 and extracts them for input to the body part regression computer model 130. The body part regression computer model 130 is an artificial intelligence (AI) computer model, such as a DNN or CNN, that is specifically trained to predict a body part regression score for a medical image (slice) based on the image features present in the medical image (slice). The body part regression computer model 130 is specifically trained, through a machine learning process, to associate body part regression (BPR) scores with medical images based on how likely the medical image is to depict one or more particular anatomical structures of interest. The BPR score is a score that represents where an axial slice is relative to one or more body landmarks, i.e., anatomical structure(s) of interest.

For example, again using the CTPA contrast phase embodiment as an example, the body part regression model 130 is trained on axial slices and their ground truth labels of BPR scores to predict BPR scores for other slices. That is, slices are annotated with BPR scores as a ground truth. The slices are input to the body part regression model 130 which predicts a BPR score for the slices. The predicted BPR scores are compared to the ground truth BPR scores to determine an error and, through a machine learning process comprising many iterations or epochs, adjustments are made to the operating parameters of the body part regression model 130 to reduce the error between the prediction and the ground truth, e.g., weights of nodes in the DNN or CNN are adjusted to reduce the error. Once the training of the model has converged such that the error is equal to or less than a predetermined level of error, or a predetermined number of epochs have elapsed, the body part regression model 130 is considered to have been trained and may then be applied to new slice data to predict a BPR score for the new slice.

Figure 2:
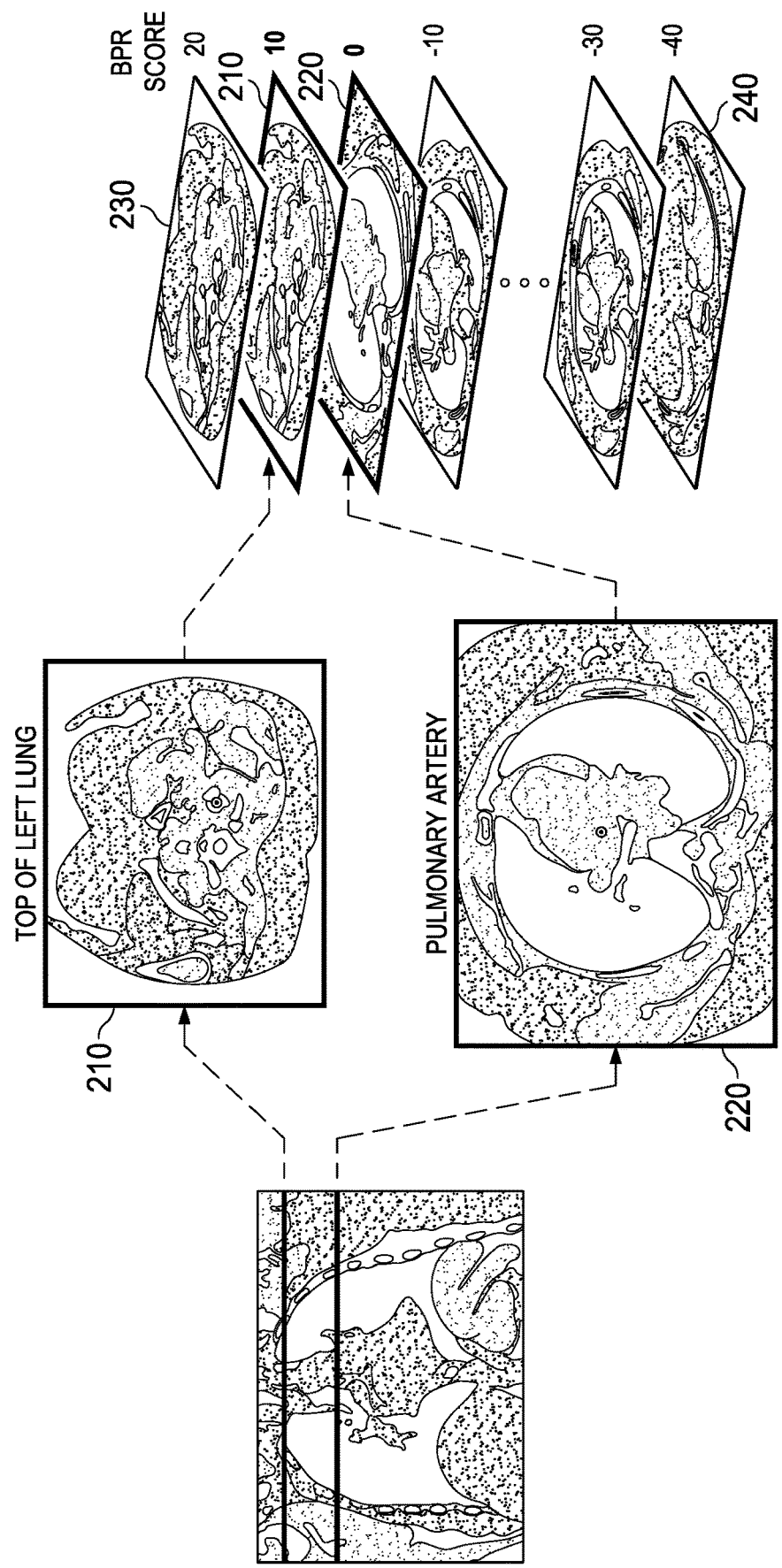
FIG. 2 is an example diagram depicting an example annotation of body part regression scores to slices of a medical imaging study, for training of a body part regression computer model, in accordance with one illustrative embodiment.

With reference to FIG. 2, in one illustrative embodiment, using again the CTPA example, the training slices are annotated with BPR scores based on the identification of two landmark slices 210 and 220, e.g., a slice representing the top of the left lung and a slice representing the pulmonary artery, with the former slice being given a body part regression score of 10 and the latter being given a body part regression score of 0. Other slices, such as slices between the two landmark slices, as indicated by slice indices being between the slice index of slice 210 and slice 220, or slices outside of the two landmark slices, i.e., slices with indices greater than that of slice 210 and lower than that of slice 220, are given linear interpolated BPR scores. Thus, for example, slice 230 is given a linearly interpolated BPR score of 20 and slice 240 is given a linearly interpolated BPR score of −30. Thus, the BPR score, in some illustrative embodiments, represents a relative distance from a slice depicting an anatomical structure of interest, e.g., pulmonary artery in this example, either above or below, however this is not required. Any scheme for assigning BPR scores may be used without departing from the spirit and scope of the illustrative embodiments as long as the BPR score scheme is devised to be able to distinguish between slices having anatomical structures of interest for at least one contrast phase of interest.

By performing a machine learning training operation on the body part regression computer model 130 using a training data set comprising slices with corresponding annotated BPR scores, the body part regression computer model 130 learns to associate slice features with BPR scores. That is, patterns of pixel intensities, or gray scale coloring, values in the slice data, which may be represented as HU values or CT number values for example, may be associated with BPR scores such that when particular patterns are determined to be present, the body part regression computer model 130 generates a probability that the slice has a particular BPR score and the highest probability BPR score will be selected as the predicted BPR score for the input slice. Thus, a trained body part regression computer model 130 is generated and implemented in computer logic specially configured through a machine learning process.

With reference again to FIG. 1, having trained the body part regression computer model 130 to predict the BPR scores for medical images (slices) using a machine learning training operation, one example of which is described above with regard to FIG. 2, the body part regression computer model 130 may be applied to input slices, such as the subset of slices 125 extracted from the medical imaging study data structure 110, to predict BPR scores for each of the extracted slices. The body part regression model 130 may further comprise logic that takes the predicted BPR scores for the extracted slices 125 and performs a linear regression on the predicted BPR scores. This linear regression fits a line to the predicted BPR scores as shown in the plot 135 in FIG. 1 by interpolating BPR scores for each of the slice indices in the medical imaging study data structure 110. The line correlates BPR score (vertical axis) with slice index (horizontal index). From this line, and known BPR scores for slices depicting anatomical structures of interest, a slice in the medical imaging study data structure 110 that is most likely to have the anatomical structures of interest depicted can be predicted as a slice along the line that has a BPR score closest to the known BPR score for the anatomical structure of interest.

For example, assume that a BPR score scale is established in which a BPR score of 0 represents a slice depicting the pulmonary artery and 10 represents the top of the left lung. Using this BPR score scale, annotated slices based on this BPR score scale may be evaluated to determine a median BPR score for a particular anatomical structure of interest. For example, it may be determined by looking at 1500 annotated slices that the median BPR score for the pulmonary artery is not in fact 0 but rather 0.02, and the BPR score for another anatomical structure, e.g., the top of the left lung, is 10.02. The known BPR scores, determined from evaluation of the median BPR scores in annotated slices, or through other means such as other statistical measures of BPR scores, or even subject matter expert (SME) assigning of known BPR scores and the like, may be stored in a data structure of the representative slice selection engine 140 for use in selecting a representative slice from the linear regression of the predicted BPR scores.

Thus, the body part regression model 130 predicts BPR scores for input slices 125 and generates a linear regression of the predicted BPR scores, such as depicted as 135 in FIG. 1, for example. The representative slice selection engine 140 applies the known BPR score for a slice determined to most likely depict an anatomical structure of interest, to select a representative slice from the medical imaging study data structure 110 for further processing in a second stage of operation 147 of the processing pipeline 100. For example, a known BPR score for a slice depicting the pulmonary trunk may be used to compare to the linear regression and select a point along the line having a BPR score closest to the known BPR score for a slice depicting the pulmonary trunk. The corresponding slice index is determined from the plot 135 and the corresponding slice having the identified slice index is then selected and extracted from the medical imaging study data structure 110 as the representative slice for further processing.

Figure 3A:
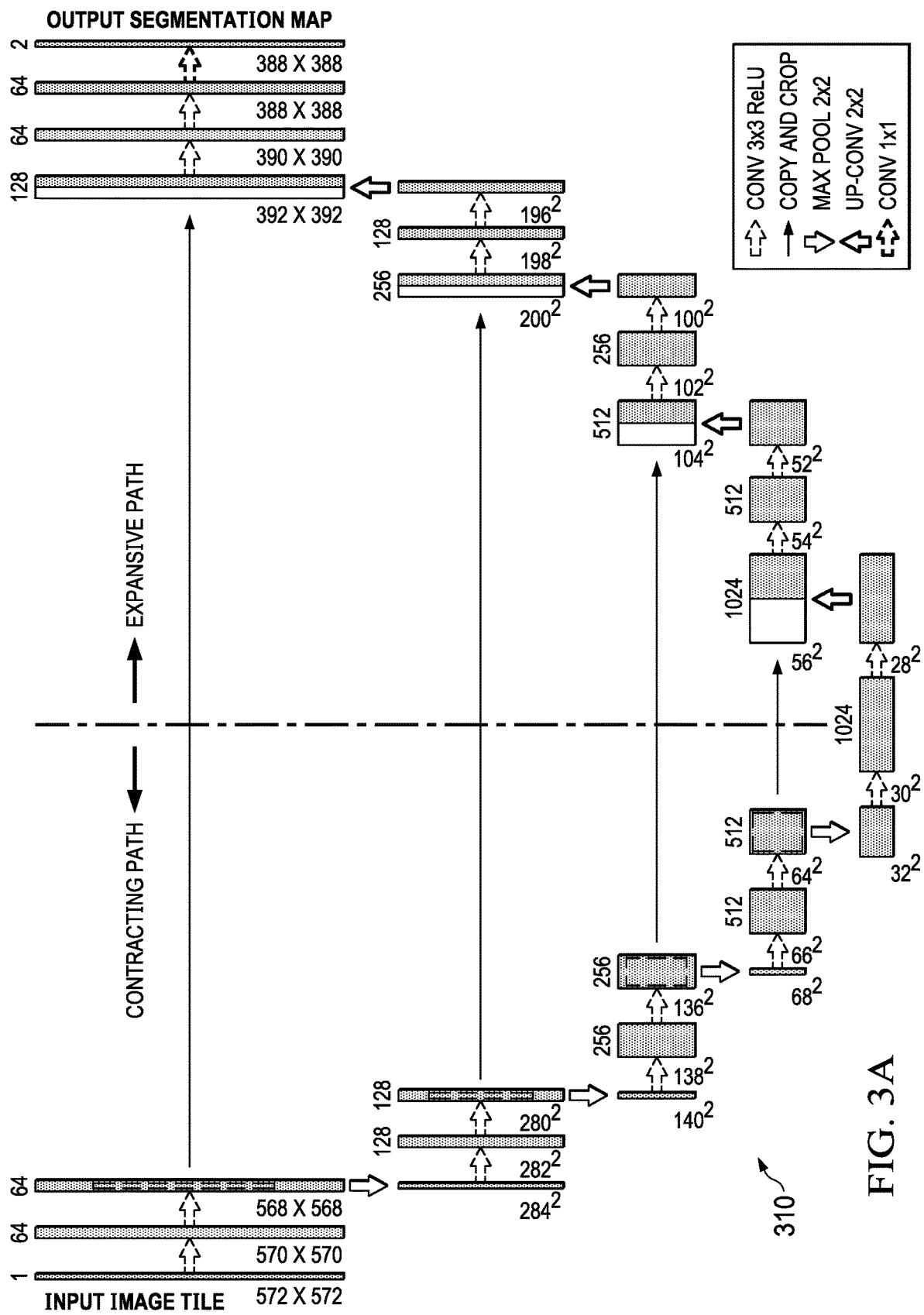
FIG. 3A is an example diagram illustrating a trained segmentation model in accordance with one illustrative embodiment.
Figure 3B:
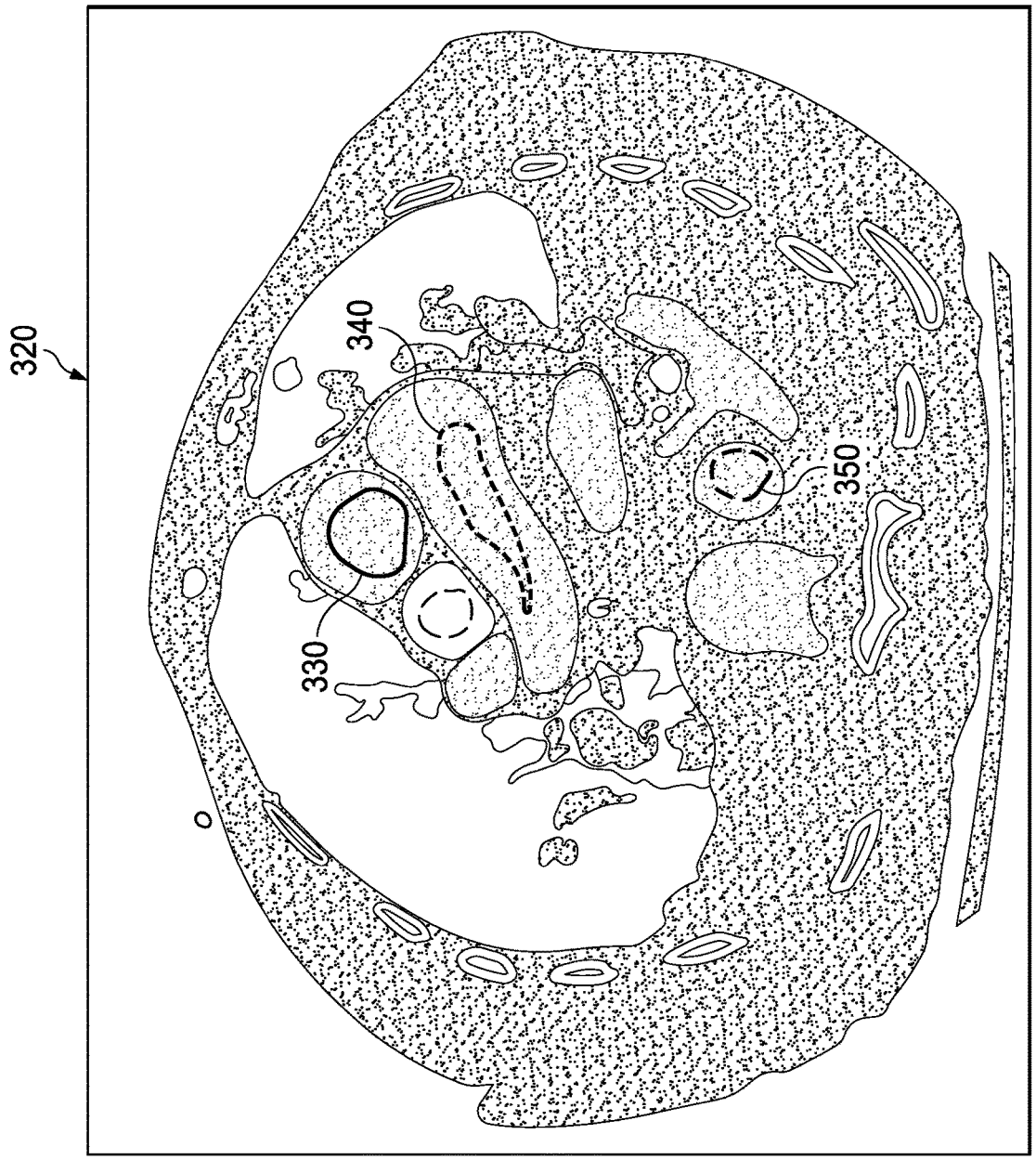
FIG. 3B is an example of a segmentation result for a trained segmentation model in accordance with one illustrative embodiment.

The representative slice selected based on the linear regression and known BPR scores for medical images having anatomical structures of interest, is provide as input to a second stage of operation 147 of the processing pipeline 100 that comprises the segmentation computer model 150 and the HU value computation and evaluation engine 160. The segmentation computer model 150 is a trained medical image segmentation model which segments the medical image with regard to anatomical structures of interest, e.g., SVC, ascending aorta, descending aorta, pulmonary artery, etc. For example, the segmentation computer model 150 may be a trained U-Net computer model, such as shown in FIG. 3A. As shown in FIG. 3A, for a CTPA medical imaging study analysis, the U-Net 310, which is a CNN, is trained with axial slices where the pulmonary trunk is represented in the axial slices. In each slice, four vessel regions, e.g., the ascending aorta, descending aorta, SVC, and pulmonary artery, are annotated and the U-Net model is trained to segment these regions. Segmentation of anatomical structures in medical images is generally known in the art and thus, a more detailed description is not provided herein. The segmentation, as shown in FIG. 3B, results in contours 330-350 or outlines of anatomical structures that are depicted in the slice 320 (also shown in the segmented slice 155 in FIG. 1). These contours or outlines surround pixels of the segmented slice 155, where these pixels have corresponding HU values or CT numbers (represented in the depicted image as grayscale images), as determined from the medical imaging equipment and provided in the medical imaging study data structure.

Thus, the HU values/CT numbers associated with the pixels of segmented anatomical structures, i.e. pixels within the contours 330-350, may be identified in the segmented slice 155. The HU value computation and evaluation engine 160 generates, for each segmented anatomical structure in the representative slice, e.g., each anatomical structure corresponding to a contour 330-350, a statistical measure of the HU values/CT numbers of pixels corresponding to the segmented anatomical structure. In one illustrative embodiment, the statistical measure is the median HU value, although other statistical measures may also be used, such as the mean HU value or the like. Thus, the illustrative embodiments provide an automated mechanism for generating HU values for different anatomical structures using a relatively small subset of selected medical image slices from a medical imaging data structure, such that the processing of medical imaging study data structures may be largely improved through the reduction of processing resources and time required to process the medical imaging study data structure, e.g., in some illustrative embodiments, rather than processing 400 slices, the illustrative embodiments need only process 9 slices to generate HU values for anatomical structures of interest.

In some illustrative embodiments, having generated the statistical measure of the HU value, e.g., median HU value, these values may be compared to one or more ranges or thresholds of HU value corresponding to determinations of levels of contrast material enhancement within slices. Based on the comparison, a determination is made as to whether the segmented anatomical structures in the representative slice (which again is a slice from the medical imaging study data structure 110 that is determined to most likely have the anatomical structures of interest depicted as determined based on the linear regression of the predicted body part regression scores) have sufficient contrast material enhancement to result in accurate processing of the medical imaging study data structure 110 by a corresponding trained CAD system 170 or not. That is, for example, if the median HU value equals or exceeds the predetermined threshold, then there is sufficient enhancement in the representative slice to indicate that the medical imaging study data structure 110 comprises contrast material enhanced slices for a particular contrast material phase, e.g., CTPA contrast phase, to enhance anatomical structures and potential anomalies in such anatomical structures such that the CAD system 170 is able to generate accurate results. In such cases, the medical imaging study data structure 110 as a whole may be input to the CAD system 170 for processing, or at least a portion of the medical imaging study data structure 110 may be input to the CAD system 170 for processing. For example, in some illustrative embodiments, a predetermined range of indices around the representative slice, e.g., a predetermine number of slices greater/lesser in index number, may be selected in order to select a subset of slices from the medical imaging study data structure 110 for further processing by the CAD system 170, e.g., 20 slices before and after the slice index for the representative slice may be selected in the sequence of axial slices, so as to concentrate the CAD system 170 processing on a portion of the medical imaging study data structure 110 that has the medical images that correspond to a desired contrast material phase.

If the comparison indicates that there is insufficient enhancement, then an appropriate notification 180 may be output to a computing device, display device, or the like, to inform a human user that the accuracy of processing of the medical imaging study data structure 110 by a CAD system 170 may result in low accuracy results, e.g., incorrect diagnosis. In such cases, the medical imaging study data structure 110 may not be input to the CAD system 170 for processing unless human user instruction is provided in response to the notification indicating that the user wishes to continue the processing of the medical imaging study data structure 110 by the CAD system 170. Thus, the processing pipeline 100 may operate as a pre-processing pipeline 100 that determines whether the CAD system 170 is likely to generate accurate results or not based on the predictions made by the mechanisms of the processing pipeline 100 using the particular mechanisms and methodology described above.

In some illustrative embodiments, the mechanisms and processing pipeline process described above may be performed with regard to various different anatomical structures of interest, different contrast material phases of interest, and the like, and the corresponding results of the evaluation may be used to route the medical imaging study to an appropriate CAD system 170 in a plurality of CAD systems 170. For example, there may be two CAD systems 170 provided, one for processing CTA medical imaging studies and one for CTPA medical imaging studies. The medical imaging study data structure 110 may be provided which does not specify in the metadata of the medical imaging study data structure 110 what the contrast phase(s) is/are for the medical imaging study. The mechanism of the illustrative embodiments may evaluate the medical imaging study, by the first stage of processing 107 and second stage of processing 147 to determine if the medical imaging study data structure comprises medical images in which the anatomical structures for accurate CTA processing by a CTA CAD system are sufficiently enhanced with contrast material. Similarly, consecutively or in parallel, the mechanisms of the illustrative embodiments may evaluate the medical imaging study data structure 110, by the first and second stage processing 107 and 147 to determine if the medical imaging study data structure 110 comprises medical images in which the anatomical structures for accurate CTPA processing by a CTPA CAD system are sufficient enhanced with contrast material. Based on the results of these classifications, the medical imaging study data structure may be routed to one of the CTA or CTPA CAD systems 170 for appropriate processing.

This functionality may be implemented as separate pipelines for each for of the CAD system 170 specifically configured for the particular anatomical structures of interest and corresponding HU values. In an example parallel execution embodiment, a single slice extraction engine 120 may be used to extract a subset of slices from the medical imaging study data structure 110, and the same extracted subset of slices may be processed in parallel by these parallel processing pipelines comprising the remainder of the first stage and second stage processing logic 107, 147. Alternatively, a single processing pipeline may be implemented with processing at each stage being performed repeatedly for different contrast material phase and/or anatomical structures of interest. In such a case, different representative slices for different contrast material phases and/or anatomical structures of interest may be selected by the representative slice selection logic 140, segmented by the segmentation model 150, and used as a basis for computing and evaluating HU values for anatomical structures of interest. Based on the comparison of the statistical measure of HU values for anatomical structures, a classification of the medical imaging study data structure 110 with regard to contrast material phase may be performed. For example, for a first representative slice, selected for a CTA contrast phase, it may be determined that there is insufficient contrast material enhancement, but for a second representative slice, selected for a CTPA contrast phase, it may be determined that there is sufficient contrast material enhancement for a CTPA CAD system because the pulmonary trunk is enhanced in the representative slice. Thus, the medical imaging study data structure 110 may be automatically determined to be associated with a CTPA imaging study and the medical imaging study data structure 110 may be routed to the CTPA CAD system for further processing. Moreover, the metadata of the medical imaging study data structure 110 may be updated to include an explicit identification of the medical imaging study data structure 110 as having a contrast phase of CTPA contrast phase.

In addition, it should be appreciated that this process may be repeated for subsets of medical images within the medical imaging study data structure 110. That is, in a single medical imaging study data structure 110, there may be medical images taken for various portions of the patient's body which correspond to different contrast phases, but without the particular contrast phases identified in the metadata of the medical imaging study data structure 110, e.g., there may be a first subset of medical images that correspond to a CTA contrast phase and a second subset of medical images that correspond to a CTPA contrast phase. As the medical imaging is performed with contrast material in a continuous manner, it is not readily discernable where one contrast phase starts/ends and another starts/ends, especially when not denoted in the metadata. Thus, in some illustrative embodiments, a first subset of medical images (slices) may be selected and the above process applied to determine if the first subset of medical images comprise medical images for a particular contrast phase. The same process may then be repeated for other subsets of medical images within the medical imaging study data structure 110. Thus, if the medical imaging study data structure contains more than one contrast phase, these will be identified through the mechanisms of the illustrative embodiments and the portions of the medical imaging study data structure may be routed to appropriate CAD systems based on the determined contrast phase.

In order to perform the evaluation of the medical imaging study data structure 110 to determine whether the medical imaging study data structure comprises sufficiently enhanced medical images for processing by a subsequent CAD system, only a small portion of the medical imaging study data structure need be processed. For example, the medical imaging study data structure 110 may comprise hundreds of individual slices, e.g., approximately 200-400 slices, and only a small subset of these slices is selected, e.g., 8 slices in one example embodiment, although other numbers of slices may be used without departing from the spirit and scope of the present invention. In order to perform the evaluation of the medical imaging study data structure 110 in accordance with the illustrative embodiments, this very small set of selected slices, relative to the entire size of the medical imaging study data structure 110, are used to perform the evaluation to select a single representative slice of the medical imaging study data structure 110, e.g., select a 9$^{th}$ slice, that is the slice most likely to comprise the anatomical structures of interest to the particular contrast phase, e.g., a slice comprising the pulmonary trunk for a CTPA contrast phase or the aorta for a CTA contrast phase. Thus, rather than having to load all of the slices of the medical imaging study data structure 110 to determine if there is sufficient enhancement, or rather than having to load all of the slices and process them through the CAD system before determining that the CAD system cannot provide accurate results, the illustrative embodiments utilized a processing pipeline 100 comprising trained AI computer model(s), trained through machine learning processes, to perform linear regression to select a single medical image representative of the medical imaging study data structure which can be used to determine the HU values for segmented structures and determine if there is sufficient enhancement of anatomical structures of interest. This greatly reduces processing resource needs and greatly increases the speed of the process of determining whether accurate results may be obtained from a CAD system. Moreover, this reduces CAD system resource utilization since expenditure of such resources may be saved on medical imaging study data structures that do not have sufficient enhancement to ensure accurate results by the trained CAD system.

Figure 4:
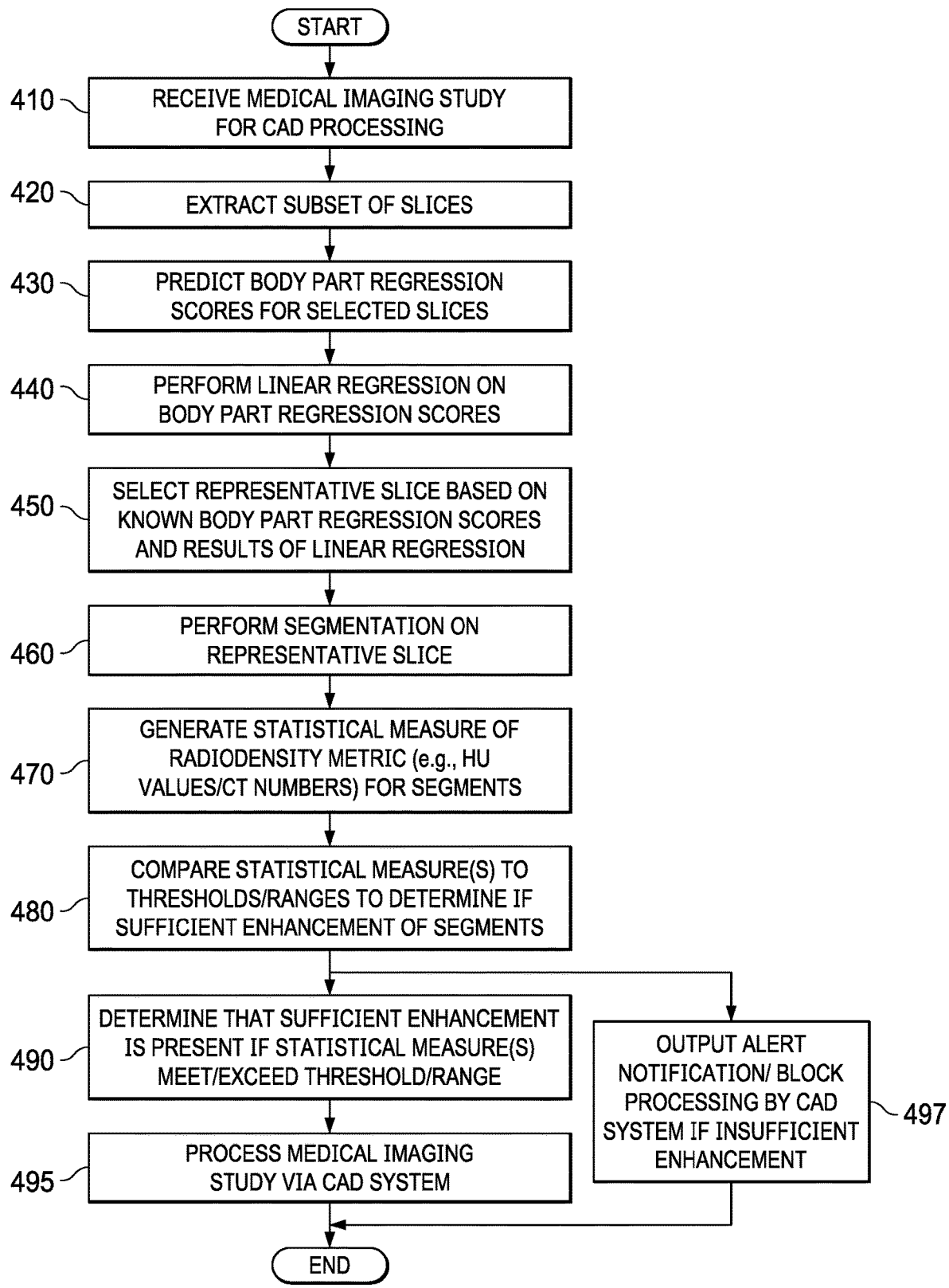
FIG. 4 is a flowchart outlining an example operation of a processing pipeline for determining HU values for anatomical structures and for determining if sufficient contrast material enhancement is present in a medical imaging study data structure for accurate processing by a computer aided diagnostic (CAD) system, in accordance with one illustrative embodiment.

FIG. 4 is a flowchart outlining an example operation of a processing pipeline for determining HU values for anatomical structures and for determining if sufficient contrast material enhancement is present in a medical imaging study data structure for accurate processing by a computer aided diagnostic (CAD) system, in accordance with one illustrative embodiment. As shown in FIG. 4, the operation starts by receiving a medical imaging study data structure for processing by a CAD system (step 410). Slice extraction engine selects and extracts a subset of slices from the medical imaging study data structure (step 420). Preferably, the subset of slices comprises slices that are evenly distributed across a predetermined range of slices of the medical imaging study data structure, e.g., if the medical imaging study comprises 200 slices, 8 slices may be selected where each selected slice is approximately 25 slices away from a previous slice in the sequence of slice indices, e.g., slice 0, 25, 50, 75, 100, 125, 150, and 175.

For each selected slice, the slice is processed through a trained body part regression computer model to predict the body part regression score, e.g., body part regression score, for the slice (step 430). The resulting set of predicted body part regression scores are then processed using a linear regression to interpolate body part regression scores for the non-selected slices of the medical imaging study data structure (step 440). Based on known body part regression scores for anatomical structures of interest, e.g., pulmonary trunk, a slice along the line of the linear regression having a body part regression score closest to the known body part regression score for the anatomical structure of interest is selected and the corresponding slice index is identified (step 450).

The selected representative slice is the processed by a trained segmentation model to generate segmented anatomical structures in the representative slice (step 460). A statistical measure of the HU values (or CT numbers) of the pixels corresponding to the anatomical structures is generated for each anatomical structure (step 470). These statistical measures are compared to thresholds or ranges of HU values/CT numbers to determine if the thresholds are met or the statistical measure is within the given range (step 480). If so, then sufficient contrast material enhancement is determined to be present (step 490). If sufficient contrast material enhancement is found to be present, the medical imaging study data structure is sent to a corresponding CAD system for processing (step 495). Otherwise, an alert notification is output to a computing device associated with a human user to inform them of the likelihood of inaccurate results being generated by a CAD system and, in some illustrative embodiments, the medical imaging study data structure may not be input to the CAD system for processing (step 497). The operation then terminates.

As described above, the illustrative embodiments of the present invention are specifically directed to an improved computing tool that automatically selects a medical image, or slice, from a medical imaging study data structure comprising a plurality of medical imaging slices, e.g., a scan, and then performs segmentation and HU value evaluations which may be used to determine whether, and how, to route the medical imaging study data structure to an appropriate CAD system. The functions of the illustrative embodiments as described herein are intended to be performed using automated processes without human intervention. While a human being, e.g., a patient, may be the subject of the medical imaging, the illustrative embodiments of the present invention are not directed to actions performed by the patient, but rather logic and functions performed specifically by the improved computing tool on the medical images taken of the patient. Moreover, even though the present invention may provide an output to a CAD system that ultimately assists human beings in evaluating the medical condition of the patient, the illustrative embodiments of the present invention are not directed to actions performed by the human being viewing the results of the processing performed by the CAD system, but rather to the specific operations performed by the specific improved computing tool of the present invention which facilitate the processing by the CAD system in an improved manner and ultimately the generation of the results of the CAD system processing that assists the human being. Thus, the illustrative embodiments are not organizing any human activity, but are in fact directed to the automated logic and functionality of an improved computing tool.

Figure 5:
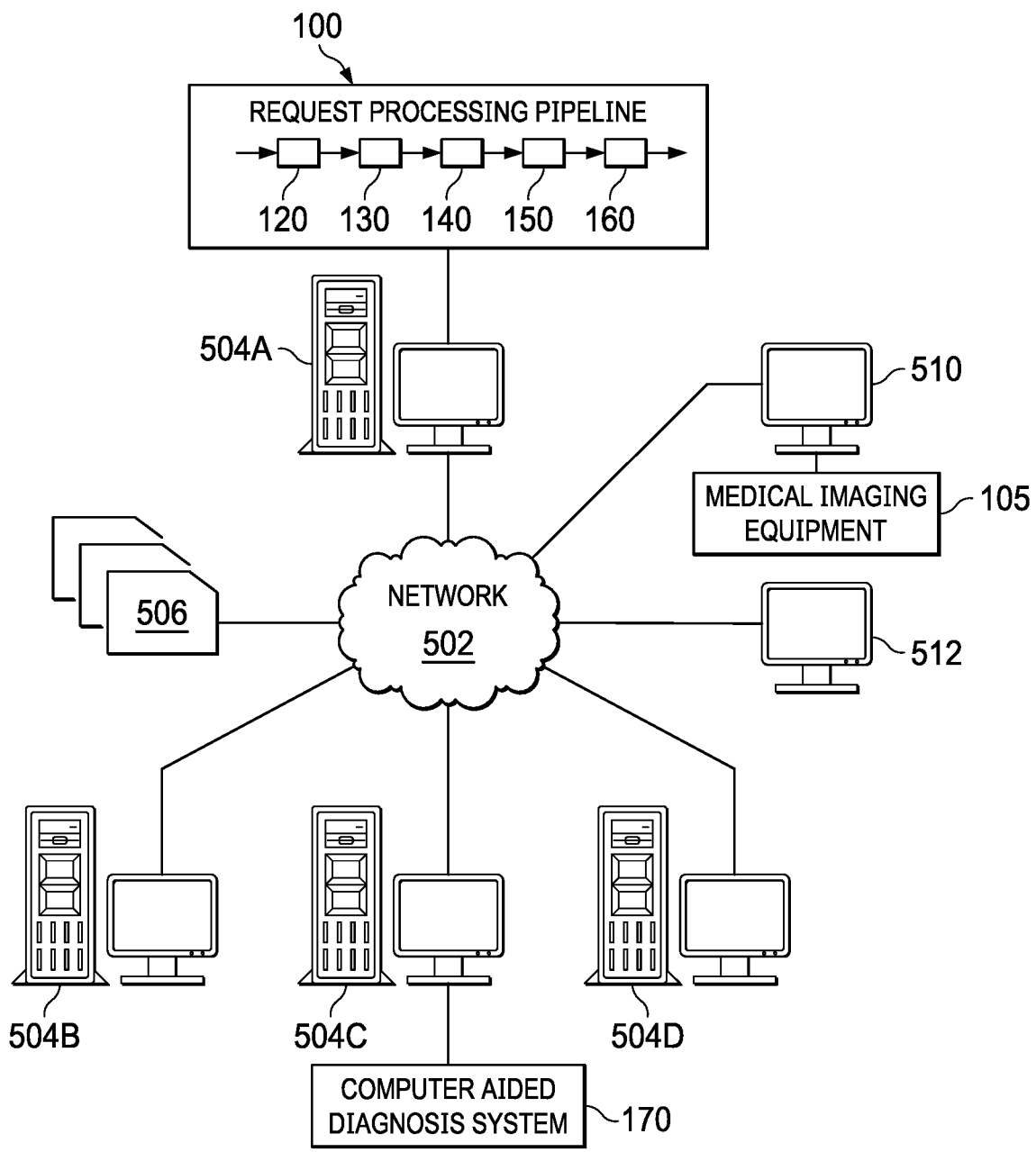
FIG. 5 is an example diagram of a distributed data processing system in which aspects of the illustrative embodiments may be implemented.
Figure 6:
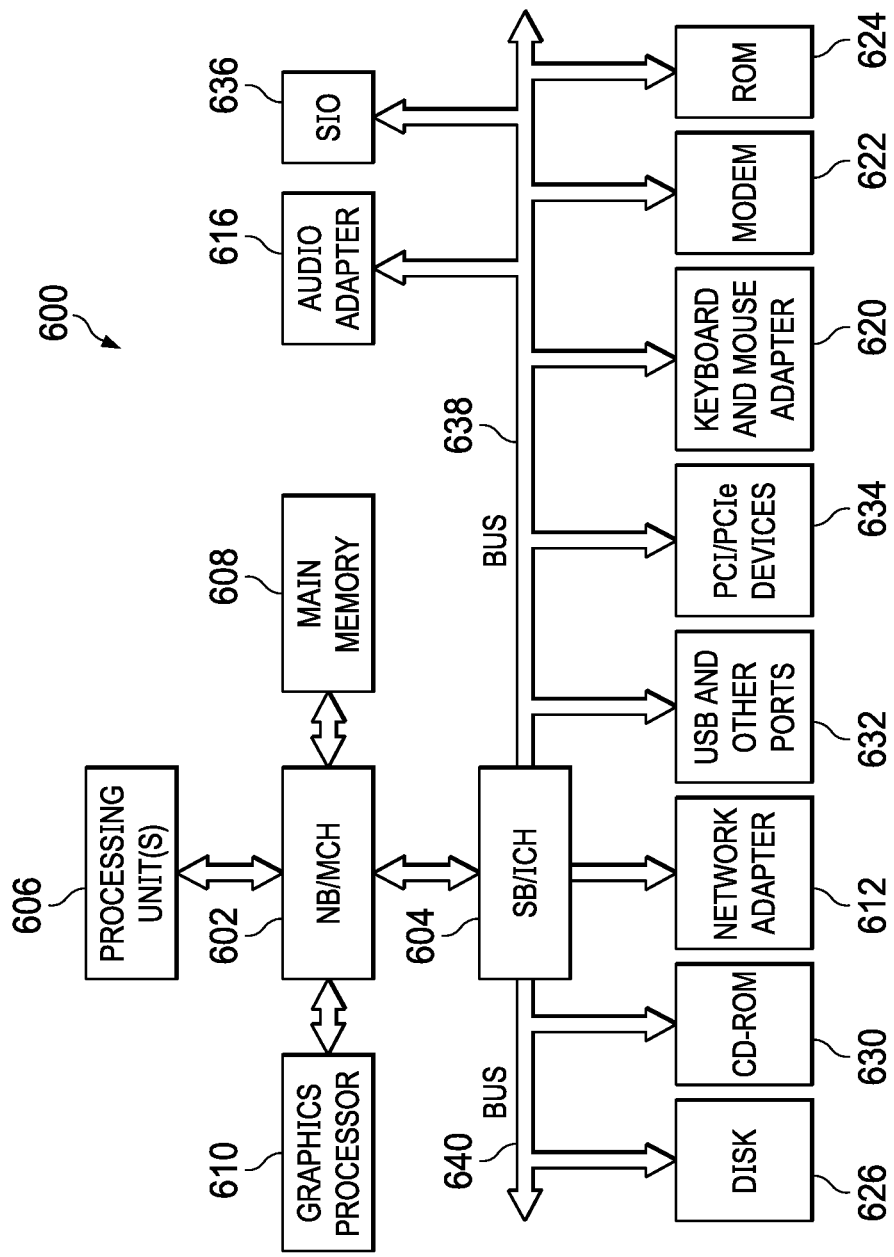
FIG. 6 is an example block diagram of a computing device in which aspects of the illustrative embodiments may be implemented.

Thus, the illustrative embodiments may be utilized in many different types of data processing environments. In order to provide a context for the description of the specific elements and functionality of the illustrative embodiments, FIGS. 5 and 6 are provided hereafter as example environments in which aspects of the illustrative embodiments may be implemented. It should be appreciated that FIGS. 5 and 6 are only examples and are not intended to assert or imply any limitation with regard to the environments in which aspects or embodiments of the present invention may be implemented. Many modifications to the depicted environments may be made without departing from the spirit and scope of the present invention.

FIG. 5 depicts a pictorial representation of an example distributed data processing system in which aspects of the illustrative embodiments may be implemented. Distributed data processing system 500 may include a network of computers in which aspects of the illustrative embodiments may be implemented. The distributed data processing system 500 contains at least one network 502, which is the medium used to provide communication links between various devices and computers connected together within distributed data processing system 500. The network 502 may include connections, such as wire, wireless communication links, or fiber optic cables.

In the depicted example, servers 504A-D are connected to network 502 along with corpus storage systems 506, where the corpus may comprise electronic documents used by computer aided diagnostic (CAD) systems or the like, to perform their functions, and storage unit 508. In addition, clients 510, 512, and 514 are also connected to network 502. These clients 510, 512, and 514 may be, for example, personal computers, network computers, or the like. In the depicted example, one or more of servers 504A-D provide data, such as boot data structures, operating system images, and applications to the clients 510-512. Clients 510-512 are clients to servers 504A-D in the depicted example. Distributed data processing system 500 may include additional servers, clients, and other devices not shown.

In the depicted example, distributed data processing system 500 is the Internet with network 502 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 500 may also be implemented to include a number of different types of networks, such as for example, an intranet, a local area network (LAN), a wide area network (WAN), or the like. As stated above, FIG. 5 is intended as an example, not as an architectural limitation for different embodiments of the present invention, and therefore, the particular elements shown in FIG. 5 should not be considered limiting with regard to the environments in which the illustrative embodiments of the present invention may be implemented.

It should be appreciated that the computing devices depicted in FIG. 5 may provide hardware and underlying firmware and software to facilitate some generic processes, such as booting the computing device to state that it may execute software (BIOS and operating system for example) may provide some standard software libraries and routines for performing various fundamental operations, such as loading data, communicating data, and processing data, the mechanisms of the improved computing tool of the illustrative embodiments is not directed to these fundamental mechanism or operations, and is not merely using these mechanisms and operations as tools. To the contrary, the present invention is directed to a specific configuring of these computing devices, through dedicated hardware and/or software executed on hardware, to implement the particular computer technology mechanisms, e.g., trained machine learning computer models and logic performing specific operations as described previously, which are not routine, conventional, or well-known operations.

In particular, as shown in FIG. 5, one or more of the computing devices, e.g., server 504A, may be specifically configured to implement one or more processing pipelines 100 such as shown in FIG. 1 and described above with regard to one or more of the illustrative embodiments. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 504A, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described herein, the implementation of the mechanisms of the illustrative embodiments improves the functionality of the computing device and provides a useful and concrete result that facilitates processing of a medical imaging study data structure to determine HU values/CT numbers for anatomical structures of interest to a particular contrast material phase of interest and a determination, based on a level of enhancement determined from these HU values/CT numbers, of whether a subsequent CAD system will be able to generate accurate results.

For example, a client computing device 510 may comprise a computing system associated with medical imaging equipment 105 and may provide a medical imaging study data structure 110 to the server 504A implementing a processing pipeline 100 such as shown in FIG. 1. The processing pipeline 100 may perform first and second stage processing of the medical imaging study data structure 110 in the manner described previously with regard to one or more illustrative embodiments, to extract a subset of slices from the medical imaging study data structure 110 which are then used to perform linear regression on predicted body part regression scores, which in turn is used to select a representative slice from the medical imaging study data structure 110 that most likely has an anatomical structure of interest represented in the selected slice. The pipeline 100 then processes this representative slice to determine a statistical measure of HU values/CT numbers for segmented anatomical structures in the representative slice and compares them to thresholds or ranges of values to determine if sufficient enhancement is present to result in accurate processing by a downstream CAD system 170, which may be implemented on the same or a different server 504A, for example. The pipeline 100 may then send the medical imaging study data structure 110 to the CAD system 170 if it is determined that sufficient enhancement is present, or may send an alert notification to a computing device of a human user if sufficient enhancement is determined to not be present, e.g., client computing device 510 or other client computing device 512. Of course other functions such as previously described above with regard to one or more of FIGS. 1-4 may also be performed.

Thus, while the hardware elements of computing devices may resemble other known computing devices, the configuration of these computing devices to specifically implement the particular mechanisms of the illustrative embodiments and to perform the particular non-generic computing operations specifically described as being particular to the illustrative embodiments, renders these computing devices as non-generic computing devices and instead are specific to the illustrative embodiments. The mechanisms of the illustrative embodiments utilize these specifically configured computing devices, or data processing systems, to perform the operations for processing a medical imaging study data structure to determine HU values/CT numbers for anatomical structures and for determining if sufficient contrast material enhancement is present for a particular contrast material phase for accurate processing by a CAD system.

These computing devices, or data processing systems, may comprise various hardware elements which are specifically configured, either through hardware configuration, software configuration, or a combination of hardware and software configuration, to implement one or more of the systems/subsystems described herein.

FIG. 6 is a block diagram of just one example data processing system in which aspects of the illustrative embodiments may be implemented. Data processing system 600 is an example of a computer, such as server 504 in FIG. 5, in which computer usable code or instructions implementing the processes and aspects of the illustrative embodiments of the present invention may be located and/or executed so as to achieve the operation, output, and external effects of the illustrative embodiments as described herein.

In the depicted example, data processing system 600 employs a hub architecture including north bridge and memory controller hub (NB/MCH) 602 and south bridge and input/output (I/O) controller hub (SB/ICH) 604. Processing unit 606, main memory 608, and graphics processor 610 are connected to NB/MCH 602. Graphics processor 610 may be connected to NB/MCH 602 through an accelerated graphics port (AGP).

In the depicted example, local area network (LAN) adapter 612 connects to SB/ICH 604. Audio adapter 616, keyboard and mouse adapter 620, modem 622, read only memory (ROM) 624, hard disk drive (HDD) 626, CD-ROM drive 630, universal serial bus (USB) ports and other communication ports 632, and PCI/PCIe devices 634 connect to SB/ICH 604 through bus 638 and bus 640. PCI/PCIe devices may include, for example, Ethernet adapters, add-in cards, and PC cards for notebook computers. PCI uses a card bus controller, while PCIe does not. ROM 624 may be, for example, a flash basic input/output system (BIOS).

HDD 626 and CD-ROM drive 630 connect to SB/ICH 604 through bus 640. HDD 626 and CD-ROM drive 630 may use, for example, an integrated drive electronics (IDE) or serial advanced technology attachment (SATA) interface. Super I/O (SIO) device 636 may be connected to SB/ICH 604.

An operating system runs on processing unit 606. The operating system coordinates and provides control of various components within the data processing system 600 in FIG. 6. As a client, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 600.

As a server, data processing system 600 may be, for example, an IBM eServer™ System p® computer system, Power™ processor based computer system, or the like, running the Advanced Interactive Executive (AIX®) operating system or the LINUX® operating system. Data processing system 600 may be a symmetric multiprocessor (SMP) system including a plurality of processors in processing unit 606. Alternatively, a single processor system may be employed.

Instructions for the operating system, the object-oriented programming system, and applications or programs are located on storage devices, such as HDD 626, and may be loaded into main memory 608 for execution by processing unit 606. The processes for illustrative embodiments of the present invention may be performed by processing unit 606 using computer usable program code, which may be located in a memory such as, for example, main memory 608, ROM 624, or in one or more peripheral devices 626 and 630, for example.

A bus system, such as bus 638 or bus 640 as shown in FIG. 6, may be comprised of one or more buses. Of course, the bus system may be implemented using any type of communication fabric or architecture that provides for a transfer of data between different components or devices attached to the fabric or architecture. A communication unit, such as modem 622 or network adapter 612 of FIG. 6, may include one or more devices used to transmit and receive data. A memory may be, for example, main memory 608, ROM 624, or a cache such as found in NB/MCH 602 in FIG. 6.

As mentioned above, in some illustrative embodiments the mechanisms of the illustrative embodiments may be implemented as application specific hardware, firmware, or the like, application software stored in a storage device, such as HDD 626 and loaded into memory, such as main memory 608, for executed by one or more hardware processors, such as processing unit 606, or the like. As such, the computing device shown in FIG. 6 becomes specifically configured to implement the mechanisms of the illustrative embodiments and specifically configured to perform the operations and generate the outputs described herein with regard to one or more illustrative embodiments of one or more instances of the processing pipeline 100 shown in FIG. 1.

Those of ordinary skill in the art will appreciate that the hardware in FIGS. 5 and 6 may vary depending on the implementation. Other internal hardware or peripheral devices, such as flash memory, equivalent non-volatile memory, or optical disk drives and the like, may be used in addition to or in place of the hardware depicted in FIGS. 5 and 6. Also, the processes of the illustrative embodiments may be applied to a multiprocessor data processing system, other than the SMP system mentioned previously, without departing from the spirit and scope of the present invention.

Moreover, the data processing system 600 may take the form of any of a number of different data processing systems including client computing devices, server computing devices, a tablet computer, laptop computer, telephone or other communication device, a personal digital assistant (PDA), or the like. In some illustrative examples, data processing system 600 may be a portable computing device that is configured with flash memory to provide non-volatile memory for storing operating system data structures and/or user-generated data, for example. Essentially, data processing system 600 may be any known or later developed data processing system without architectural limitation.

It should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system specially configured to implement a processing pipeline comprising a first trained machine learning model that performs body part regression processing on a medical imaging study data structure, and a second trained machine learning model that performs segmentation of a representative slice selected from the medical imaging study data structure, the method comprising:
   selecting, by a slice extraction engine of the processing pipeline, a subset of slices from the medical imaging study data structure;
   generating, by the first trained machine learning model of the processing pipeline, for each slice in the subset of slices, a corresponding body part regression score;
   performing, by the first trained machine learning model of the processing pipeline, a linear regression on the body part regression scores for the subset of slices;
   selecting, by a representative slice selection engine of the processing pipeline, a representative slice from the medical imaging study data structure based on results of the linear regression; and
   processing, by the second trained machine learning model of the processing pipeline, the representative slice to segment the representative slice and generate a statistical measure of a radiodensity metric for each segment in the representative slice.

2. The method of claim 1, wherein selecting the representative slice from the medical imaging study data structure comprises selecting a slice index, from a plurality of slice indices for slices in the medical imaging study data structure, corresponding to a slice having a body part regression score closest to a known body part regression score for a slice depicting an anatomical structure of interest, as the representative slice.

3. The method of claim 1, further comprising:
   comparing, for at least one segment in the representative slice, a corresponding statistical measure of radiodensity metric to a threshold radiodensity metric;
   determining whether or not sufficient enhancement by a contrast material is present in the representative slice in response to results of the comparison; and
   generating an output based on results of determining whether sufficient enhancement by a contrast material is present or not in the representative slice.

4. The method of claim 3, wherein determining whether or not sufficient enhancement by a contrast material is present in the representative slice further comprises:
   determining that sufficient enhancement is present in response to the comparison indicating that the statistical measure of radiodensity metric meets or exceeds the threshold radiodensity metric; and
   determining that insufficient enhancement is present in response to the comparison indicating that the statistical measure of radiodensity metric does not meet or exceed the threshold radiodensity metric.

5. The method of claim 4, wherein in response to the determination indicating that there is sufficient enhancement, generating the output comprises inputting at least a portion of the medical imaging study data structure to a downstream computer aided diagnosis (CAD) computing system for processing of the at least a portion of the medical imaging study data structure.

6. The method of claim 5, wherein the downstream CAD computing system is one of a plurality of downstream CAD computing systems, each CAD computing system in the plurality of downstream CAD computing systems comprising a corresponding trained machine learning computer model trained to perform computer aided diagnosis evaluations for different anatomical structures.

7. The method of claim 5, wherein the at least a portion of the medical imaging study data structure comprises a sub-portion of indexed slices in the medical imaging study data structure, less than a total number of indexed slices in the medical imaging study data structure, wherein the sub-portion comprises a predetermined number of slices having indices greater than or lower than an index of the representative slice.

8. The method of claim 4, wherein in response to the determination indicating that there is not sufficient enhancement, generating the output comprises generating an alert notification to a computing device or display device to output a notification indicating that processing of the medical imaging study data structure by a downstream computer aided diagnosis computing system will generate inaccurate results due to insufficient contrast material enhancement.

9. The method of claim 3, wherein generating the output based on results of determining whether sufficient enhancement by a contrast material is present or not in the representative slice further comprises classifying the medical imaging study data structure into one of a plurality of contrast phase classifications based on the results of determining whether sufficient enhancement by a contrast material is present or not.

10. The method of claim 1, wherein the body part regression score for a given slice is a value indicative of a relative physical distance between the given slice and a slice comprising a depiction of an anatomical structure of interest.

11. A computer program product comprising a computer readable storage medium having a computer readable program stored therein, wherein the computer readable program, when executed on a computing system, causes the computing system to:
   select, by a slice extraction engine of a processing pipeline executing in the computing system, a subset of slices from a medical imaging study data structure;
   generate, by a first trained machine learning model of the processing pipeline, for each slice in the subset of slices, a corresponding body part regression score;
   performing, by the first trained machine learning model of the processing pipeline, a linear regression on the body part regression scores for the subset of slices;
   selecting, by a representative slice selection engine of the processing pipeline, a representative slice from the medical imaging study data structure based on results of the linear regression; and
   processing, by a second trained machine learning model of the processing pipeline, the representative slice to segment the representative slice and generate a statistical measure of a radiodensity metric for each segment in the representative slice.

12. The computer program product of claim 11, wherein selecting the representative slice from the medical imaging study data structure comprises selecting a slice index, from a plurality of slice indices for slices in the medical imaging study data structure, corresponding to a slice having a body part regression score closest to a known body part regression score for an anatomical structure of interest, as the representative slice.

13. The computer program product of claim 11, wherein the computer readable program further causes the computing system to:
   compare, for at least one segment in the representative slice, a corresponding statistical measure of radiodensity metric to a threshold radiodensity metric;
   determine whether or not sufficient enhancement by a contrast material is present in the representative slice in response to results of the comparison; and
   generate an output based on results of determining whether sufficient enhancement by a contrast material is present or not in the representative slice.

14. The computer program product of claim 13, wherein the computer readable program further causes the computing system to determine whether or not sufficient enhancement by a contrast material is present in the representative slice at least by:
   determining that sufficient enhancement is present in response to the comparison indicating that the statistical measure of radiodensity metric meets or exceeds the threshold radiodensity metric; and
   determining that insufficient enhancement is present in response to the comparison indicating that the statistical measure of radiodensity metric does not meet or exceed the threshold radiodensity metric.

15. The computer program product of claim 14, wherein in response to the determination indicating that there is sufficient enhancement, the computer readable program further causes the computing system to generate the output at least by inputting at least a portion of the medical imaging study data structure to a downstream computer aided diagnosis (CAD) computing system for processing of the at least a portion of the medical imaging study data structure.

16. The computer program product of claim 15, wherein the downstream CAD computing system is one of a plurality of downstream CAD computing systems, each CAD computing system in the plurality of downstream CAD computing systems comprising a corresponding trained machine learning computer model trained to perform computer aided diagnosis evaluations for different anatomical structures.

17. The computer program product of claim 15, wherein the at least a portion of the medical imaging study data structure comprises a sub-portion of indexed slices in the medical imaging study data structure, less than a total number of indexed slices in the medical imaging study data structure, wherein the sub-portion comprises a predetermined number of slices having indices greater than or lower than an index of the representative slice.

18. The computer program product of claim 14, wherein in response to the determination indicating that there is not sufficient enhancement, the computer readable program further causes the computing system to generate the output at least by generating an alert notification to a computing device or display device to output a notification indicating that processing of the medical imaging study data structure by a downstream computer aided diagnosis computing system will generate inaccurate results due to insufficient contrast material enhancement.

19. The computer program product of claim 13, wherein generating the output based on results of determining whether sufficient enhancement by a contrast material is present or not in the representative slice further comprises classifying the medical imaging study data structure into one of a plurality of contrast phase classifications based on the results of determining whether sufficient enhancement by a contrast material is present or not.

20. An apparatus comprising:
   a processor; and
   a memory coupled to the processor, wherein the memory comprises instructions which, when executed by the processor, cause the processor to:
   select, by a slice extraction engine of a processing pipeline executing in the computing system, a subset of slices from a medical imaging study data structure;
   generate, by a first trained machine learning model of the processing pipeline, for each slice in the subset of slices, a corresponding body part regression score;
   performing, by the first trained machine learning model of the processing pipeline, a linear regression on the body part regression scores for the subset of slices;
   selecting, by a representative slice selection engine of the processing pipeline, a representative slice from the medical imaging study data structure based on results of the linear regression; and
   processing, by a second trained machine learning model of the processing pipeline, the representative slice to segment the representative slice and generate a statistical measure of a radiodensity metric for each segment in the representative slice.

* * * * *